US008748135B2

(12) United States Patent
Gilbert et al.

(10) Patent No.: US 8,748,135 B2
(45) Date of Patent: Jun. 10, 2014

(54) α-1,4-GALACTOSYLTRANSFERASE (CGTD) FROM *CAMPYLOBACTER JEJUNI*

(71) Applicant: National Research Council of Canada, Ottawa (CA)

(72) Inventors: Michel Gilbert, Gatineau (CA); Warren Wakarchuk, Ottawa (CA); Scott Houliston, Ottawa (CA)

(73) Assignee: National Research Council of Canada, Ottawa, Ontario (CA)

( * ) Notice: Subject to any disclaimer, the term of this patent is extended or adjusted under 35 U.S.C. 154(b) by 0 days.

(21) Appl. No.: 13/687,944

(22) Filed: Nov. 28, 2012

(65) Prior Publication Data

US 2013/0089896 A1 Apr. 11, 2013

Related U.S. Application Data

(62) Division of application No. 12/299,194, filed as application No. PCT/CA2007/000745 on May 1, 2007, now abandoned.

(60) Provisional application No. 60/797,132, filed on May 2, 2006.

(51) Int. Cl.
*C12P 19/18* (2006.01)
*C12N 9/10* (2006.01)
*C07H 21/04* (2006.01)
*C07K 1/00* (2006.01)

(52) U.S. Cl.
USPC ............. 435/97; 435/193; 536/23.2; 530/350

(58) Field of Classification Search
USPC ...................... 435/97, 193; 536/23.2; 530/350
See application file for complete search history.

(56) References Cited

U.S. PATENT DOCUMENTS 5,922,577 A * 7/1999 Defrees et al. ................... 435/97
2004/0253670 A1 * 12/2004 Endo et al. .................... 435/69.1

FOREIGN PATENT DOCUMENTS

WO WO 02/077165 A2 10/2002

OTHER PUBLICATIONS

Fouts et al., Major structural differences and novel potential virulence mechanisms from the genomes of multiple *Campylobacter* species. PLoS Biology, 2005, vol. 3(1): 0072-0085.*
Zhang et al. Efficient chemoenzymatic synthesis of globotriose and its derivatives with a recombinant a-(1,4)-galactosyltransferase. Carbohydrate Res., 2002, vol. 337: 969-976.*
3 pages Definition of Glycosylation, from Dictionary and Thesaurus http://glycosylation.askdefine.com/, down-loaded Oct. 3, 2013.*
4 pages Glycosylation/Structure, down-loaded from http://www.cryst.bbk.ac.uk on Oct. 3, 2013.*
2 pages Glycosylation, down-loaded from http://www.uniprot.org/manual/carbohyd on Oct. 3, 2013.*
Antoine, T. et al., "Large Scale In Vivo Synthesis of Globotriose and Globotetraose by High Cell Density Culture of Metabolically Engineered *Escherichia coli*," *Biomiche* 87(2):197-203(2005).
Chica et al., "Semi-Rational Approaches to Engineering Enzyme Activity: Combining the Benefits of Directed Evolution and Rational Design," *Curr. Opi Biotechnol.* 16:378-384 (2005).
Coutinho, et al., "An Evolving Hierarchial Family Classification for Glycolsyltransferases," *Journal of Molecular Biology* 328(2):307-317 (2003).
Fouts et al., "Major Structural Differences and Novel Potential Virulence Mechanisms From the Genomes of Multiple *Campylobacter* Species," *PLoS Biology* 3(1):72-85 (2005).
GenBank Accession No. AAM90647 (Feb. 26, 2009).
GenBank Accession No. ABM6330 (Jan. 15, 2007).
GenBank Accession No. AF400669 (Feb. 26, 2009).
GenBank Accession No. EF176584 (Jan. 15, 2007).
GenPept Accession No. AAK85423 (Jan. 3, 2002).
Gilbert, M. et al., "The Genetic Bases for the Variation in the Lipo-Oliogosaccharide of the Mucosal Pathogen, *Campylobacter jejuni*," *J. Biol. Chem.* 277(1):327-337 (2002).
Houliston, R.S., et al., "Complete Chemoenzymatic Synthesis of the Forssman Antigen Using Novel Glycosyltransferases Identified in *Campylobacter jejuni* and *Pasteurella multocida*" *Glycobiology* 19(2):153-159 (2009).
Karylshev, A., et al., "The *Campylobacter jejuni* Glycome," *FEMS Microbiology Reviews* 29(2):377-390 (2005).
Kimchi-Sarfaty et al., "A Silent Polymorphism in the MDR1 Gene Changes Substrate Specificity," *Science* 315:525-528 (2007).
Nackley et al., "Human Caechol-O-Methytransferase Haplotypes Modulate Protein Expression by Altering MRNA Secondary Structure," *Science* 314:1930-1933 (2006).
Sauna et al., "Silent Polymorphisms Speak: How They Affect Pharmacogenomics and the Treatment of Cancer," *Cancer Research* 67(20):9609-9612 (2007).
Sen et al., "Developments in Directed Evolution for Improving Enzyme Functions," *Appl. Biochem. Biotechnol.* 143:212-223 (2007).
Zhang, J. et al.. "Efficient Chemozenzymatic Synthesis of Globotriose and Its Derivatives With a Recombinant Alpha-(1->4)-Galactosyltransferase," *Carbohydrate Research* 337(11):969-976 (2002).

* cited by examiner

*Primary Examiner* — Ganapathirama Raghu
(74) *Attorney, Agent, or Firm* — Pasternak Patent Law; Dahna S. Pasternak

(57) ABSTRACT

α-1,4-galactosyltransferase (CgtD) polypeptides, nucleic acids that encode the polypeptides, including a polypeptide from *Campylobacter jejuni* strain LIO87 have been isolated and characterized. A method of producing a galactosylated saccharide comprising contacting an acceptor saccharide containing a terminal galactose, a donor substrate comprising a galactose moiety and one of the CgtD polypeptides is described.

5 Claims, 3 Drawing Sheets

| Residue | Chemical Shift (ppm) | | | | | | | | | | | |
| --- | --- | --- | --- | --- | --- | --- | --- | --- | --- | --- | --- | --- |
| | H1 | C1 | H2 | C2 | H3 | C3 | H4 | C4 | H5 | C5 | H6 | C6 |
| βGlcNAc (a) | 5.36 | 99.2 | 4.09 | 55.8 | 3.86 | 72.9 | 3.86 | 79.2 | 3.85 | 76.1 | 4.05, 3.94 | 60.6, 60.9 |
| βGal(1-4) (b) | 4.58 | 104.1 | 3.61 | 71.8 | 3.77 | 73.0 | 4.06 | 78.1 | 3.82 | 76.3 | 3.94, 3.88 | 61.2 |
| αGal(1-4) (c) | 4.97 | 101.1 | 3.86 | 69.5 | 3.92 | 69.9 | 4.05 | 69.7 | 4.38 | 71.7 | 3.73 | 61.4 | aChemical shifts are referenced with respect to the methyl group of the internal acetone standard appearing at 2.23 and 31.1 ppm in the $^1$H and $^{13}$C dimensions respectively.

FIG. 2

```
              10         20         30         40         50         60
               |          |          |          |          |          |
AAK73187    MKQEISSFWYTPRGYKGIGLMELLSIKSFIDNGYKFILYTYNLDDKIFKKLDELFDDFEL
AAK85423    MKQEISSFWYTPRGYKGIGLMELLSIKSFIDNGYKFILYTYNLDDKIFKKLDELFDDFEL
AAM90647    -MTEISSFWYTPKGYKGIGLMEILTIKSWLDHGYKFHLYTYNLEDKIFLKFQELFDNFIL
            ********:*********:*:***:.*:.****.******.**** *::****:* *

Prim.cons.  MKQEISSFWYTPRGYKGIGLMELLSIKSFIDNGYKFILYTYNLDDKIFKKLDELFDDFEL
              70         80         90        100        110        120
               |          |          |          |          |          |
AAK73187    KDANEIVSFKNYFRDDRGSGVAAFSDYFRYNLLYLKKKKRGGVWVDLDMICLNYIDLN-E
AAK85423    KDANEIVSFKNYFRDDRGSGVAAFSDYFRYNLLYLKKKKRGGVWVDLDMICLNYIDLN-E
AAM90647    KDANEIIPFEEYFSDDRGAGVAAFSDFFRFNLLYLR----GGVWVDLDMVCLNHYDYDKK
            ******:.*::**.****:******:**:*****:    **********:***:  . :

Prim.cons.  KDANEIVSFKNYFRDDRGSGVAAFSDYFRYNLLYLKKKKRGGVWVDLDMICLNYIDLNKE
             130        140        150        160        170        180
               |          |          |          |          |          |
AAK73187    EYIFTQEVDEDNKKSRITTSFLKFSRYSDFGKNLIQEAEKIINKRKKISWGVIGPWFLAD
AAK85423    EYIFTQEVDEDNKKSRITTSFLKFSRYSDFGKNLIQEAEKIINKRKKISWGVIGPWFLAD
AAM90647    EYIFSKEIDNDLSKARITTSLLKFPKQSEFGKLIIDEAKKIVDDNKIIPWGIIGPWFLAK
            ****::::*::*..*:*****:***.:.*:***:**:***:::.*:*.**:*******.

Prim.cons.  EYIFTQEVDEDNKKSRITTSFLKFSRYSDFGKNLIQEAEKIINKRKKISWGVIGPWFLAD
             190        200        210        220        230        240
               |          |          |          |          |          |
AAK73187    HVKKCGLENFVWDYKRTCQIPWCNVKIFLDNTSIDISQPFLHLFSEMWRLNNMEKNTFHQ
AAK85423    HVKKCGLENFVWDYKRTCQIPWCNVKIFLDNTSIDISQPFLHLFSEMWRLNNMEKNTFHQ
AAM90647    WVKEYDLEKHALDYKDTCQISCGNTRDFIDKKIFDKNRLCLHLFSEMWKIYKMNKNHFYK
            ** :  :*:.. ****.****. .*:.:*:.:**.:*.::********:: ::*:*::

Prim.cons.  HVKKCGLENFVWDYKRTCQIPWCNVKIFLDNTSIDISQPFLHLFSEMWRLNNMEKNTFHQ
             250        260        270        280        290        300
               |          |          |          |          |          |
AAK73187    MGVYGQLLKKHEIEKLYNQINTCLKTS--MLDNIASFL-----TKFFIKKL--------
AAK85423    MGVYGQLLKKHEIEKLYNQINTCLKTS--MLDNIASFL-----TKFFIKKL--------
AAM90647    SCIYGFLLQKHNILDLCLKLNYNLSFCDKHYDKFLPFINIKNKIRFYFRHPKKIFKKNNA
            :..** **::**:*.::.:.* :*:.   : *:: **:     .:*::::

Prim.cons.  MGVYGQLLKKHEIEKLYNQINTCLKTSDKMLDNIASFLNIKNKTKFFIKKLKKIFKKNNA
```

Alignment data:
Alignment length : 300
Identity (*) : 160 is 53.33 %

FIG. 3

α-1,4-GALACTOSYLTRANSFERASE (CGTD) FROM *CAMPYLOBACTER JEJUNI*

CROSS-REFERENCES TO RELATED APPLICATIONS

This application claims the benefit of U.S. Provisional Application No. 60/797,132, filed May 2, 2006, which is herein incorporated by reference for all purposes.

FIELD OF INVENTION

The invention relates to α-1,4-galactosyltransferase (CgtD) polypeptides, nucleic acids that encode the polypeptides, and methods of using the polypeptides.

BACKGROUND OF THE INVENTION

Carbohydrates are now recognized as being of major importance in many cell-cell recognition events, notably the adhesion of bacteria and viruses to mammalian cells in pathogenesis and leukocyte-endothelial cell interaction through selectins in inflammation (Varki (1993) *Glycobiology* 3: 97-130). Moreover, sialylated glycoconjugates that are found in bacteria (Preston et al. (1996) *Crit. Rev. Microbiol.* 22:139-180; Reuter et al. (1996) *Biol. Chem. Hoppe-Seyler* 377:325-342) are thought to mimic oligosaccharides found in mammalian glycolipids to evade the host immune response (Moran et al. (1996) *FEMS Immunol. Med. Microbiol.* 16:105-115). Molecular mimicry of host structures by the saccharide portion of lipopolysaccharide (LPS) is considered to be a virulence factor of various mucosal pathogens, which use this strategy to evade a host immune response (Moran et al. (1996) *FEMS Immunol. Med. Microbiol.* 16: 105-115; Moran et al. (1996) *J. Endotoxin Res.* 3: 521-531).

The oligosaccharide structures involved in these and other processes are potential therapeutic agents, but they are time consuming and expensive to make by traditional chemical means. A very promising route to production of specific oligosaccharide structures is through the use of the enzymes which make them in vivo, the glycosyltransferases. Such enzymes can be used as regio- and stereoselective catalysts for the in vitro synthesis of oligosaccharides (Ichikawa et al. (1992) *Anal. Biochem.* 202: 215-238).

Large scale enzymatic synthesis of oligosaccharides depends on the availability of sufficient quantities of the required glycosyltransferases. However, production of glycosyltransferases in sufficient quantities for use in preparing oligosaccharide structures has been problematic. Expression of many mammalian glycosyltransferases has been achieved involving expression in eukaryotic hosts which can involve expensive tissue culture media and only moderate yields of protein (Kleene et al. (1994) *Biochem. Biophys. Res. Commun.* 201: 160-167; Williams et al. (1995) *Glycoconjugate J.* 12: 755-761). Expression in *E. coli* has been achieved for mammalian glycosyltransferases, but these attempts have produced mainly insoluble forms of the enzyme from which it has been difficult to recover active enzyme in large amounts (Aoki et al. (1990) *EMBO. J.* 9:3171-3178; Nishiu et al. (1995) *Biosci. Biotech. Biochem.* 59 (9): 1750-1752). Furthermore, because of the biological activity of their products, mammalian sialyltransferases generally act in specific tissues, cell compartments and/or developmental stages to create precise glycan structures. Identification of glycosyltransferases that can be used in enzymatic synthesis of commercially valuable oligosaccharides and that can be produced in large quantities would thus be useful in the development of these technologies. The present invention fulfills this and other needs.

BRIEF SUMMARY OF THE INVENTION

In one aspect the present invention provides a method of producing a galactosylated product saccharide by contacting an acceptor substrate with a donor substrate comprising a galactose moiety and an isolated or recombinant α-1,4-galactosyltransferase polypeptide with at least 80% identity to SEQ ID NO:2; and allowing transfer of a galactose moiety to the acceptor saccharide to occur, thereby producing the galactosylated product saccharide. In one embodiment the α-1,4-galactosyltransferase polypeptide comprises an amino acid sequence with at least 90% or 95% identity to SEQ ID NO:2. In another embodiment the α-1,4-galactosyltransferase polypeptide comprises an amino acid sequence of SEQ ID NO:2. In a further embodiment the method is performed at a commercial scale of production. In another embodiment the method includes a step of isolating the galactosylated product saccharide.

In another aspect the present invention provides a reaction mixture comprising an isolated or recombinant α-1,4-galactosyltransferase polypeptide that transfers a galactose moiety from a donor substrate to an acceptor substrate and that has an amino acid sequence with at least 80%, 90%, 95%, or 100% identity to SEQ ID NO:2.

In another aspect the invention provides an isolated nucleic acid that encodes an α-1,4-galactosyltransferase polypeptide. In one embodiment the isolated nucleic acid comprises a nucleic acid sequence with at least 90% or 95% identity to SEQ ID NO:1. In another embodiment the isolated nucleic acid comprises a nucleic acid sequence of SEQ ID NO:1.

In another aspect the invention provides an expression vector that includes a nucleic acid sequence with at least 80%, 90% or 95% identity with SEQ ID NO: 1. The invention also includes host cells that contain the expression vector and methods to make an α-1,4-galactosyltransferase polypeptide, by growing the host cells under conditions suitable for expression of the α-1,4-galactosyltransferase polypeptide.

BRIEF DESCRIPTION OF THE DRAWINGS

FIG. 2 provides $^1$H and $^{13}$C chemical shifts$^a$ of αGal-1,4-βGal-1,4-βGlcNAc-p-nitrophenyl.

FIG. 3 provides the alignment of the three full-length versions of CgtD (SEQ ID NOS:3, 4 and 2, respectively) using the ClustalW program. The bottom sequence is a consensus sequence (SEQ ID NO:5). The following symbols are used: "*" means that the residues or nucleotides in that column are identical in all sequences in the alignment; ":" means that conserved substitutions have been observed, as defined on the Clustal website; and "." means that semi-conserved substitutions are observed. See, e.g., www.ebi.ac.uk/clustalw/#.

DETAILED DESCRIPTION OF THE INVENTION

I. Introduction

Figure 1:
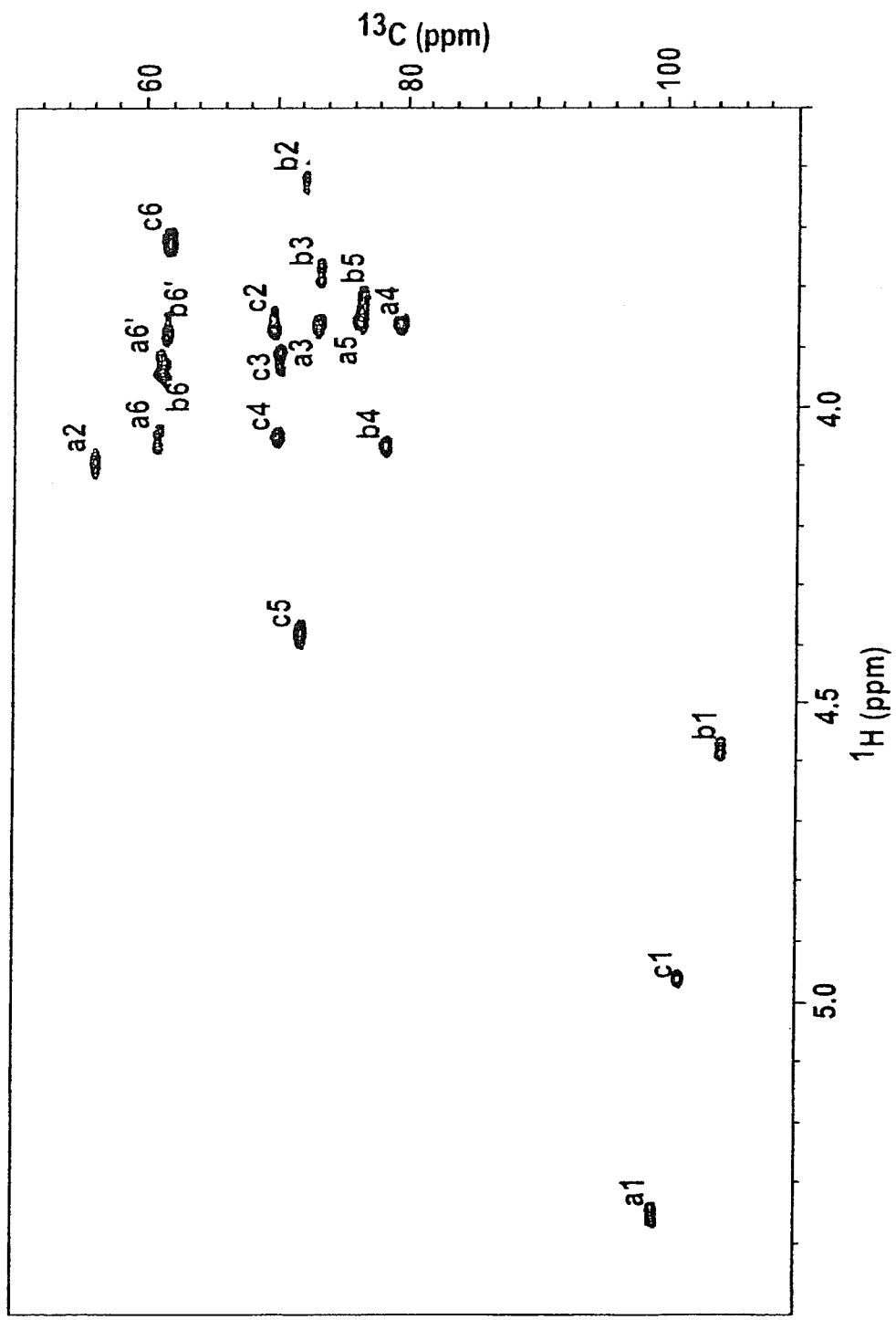
FIG. 1 provides $^1$H-$^{13}$C HSQC spectrum of αGal-1,4-βGal-1,4-βGlcNAc-p-nitrophenyl. Cross-peaks are labeled according to the lettering and numbering in FIG. 2 (i.e. a for βGlcNAc, b for βGal, and c for αGal). The carbon resonances of a4 and b4 exhibit shifts that are downfield in comparison with their value in monosaccharides, consistent with their participation in a glycosidic bond.

The lipooligosaccharide (LOS) biosynthesis locus has been sequenced in various strains of *Campylobacter jejuni* as part of a project on the comparative genomics of this locus. See, e.g., Gilbert, et al., *J. Biol. Chem.* 275:3896-3906 (2000); Gilbert, et al., *J. Biol. Chem.* 277:327-337 (2002); and Gilbert, et al., in *Campylobacter: Molecular and Cellular Biology*. (Horizon Bioscience, Editors: J. M. Ketley and M. E. Konkel), Chapter 11 (2005).

The function of some of the encoded protein has been experimentally determined. *C. jejuni* LIO87 is a serotype strain of the LIOR (heat labile) serotyping system. The organization of the LIO87 LOS locus (Class "D", GenBank accession number AF400669) is distinct from the majority of the *C. jejuni* LOS loci characterized so far (Classes "A", "B" and "C", Gilbert et al. 2002). For example, the LOS locus from *C. jejuni* LIO87 lacks the cluster of genes involved in sialic acid biosynthesis and in the expression of LOS outer cores mimicking gangliosides. The *C. jejuni* LIO87 LOS locus includes 10 open reading frames (ORFs). Sequence homology searches indicated that four of these ORFs (ORFs #1, #2, #3 and #10) are involved in the biosynthesis of the inner core or the lipid A. It was not possible to infer the function of the proteins encoded by the other six open reading frames based on sequence information.

The function of the CgtD protein was determined experimentally and the present invention demonstrates for the first time that the CgtD gene product has α-1,4-galactosyltransferase activity. In addition, the enzyme is also able to transfer galactose from a donor to either LacNAc (Gal-β-1,4-GlcNAc) or the Lac (Gal-β-1,4-Glc) derivatives as an acceptor molecule.

II. Definitions

The following abbreviations are used herein:
- Ara=arabinosyl;
- Fru=fructosyl;
- Fuc=fucosyl;
- Gal=galactosyl;
- GalNAc=N-acetylgalactosaminyl;
- Glc=glucosyl;
- GlcNAc=N-acetylglucosaminyl;
- Man=mannosyl; and
- NeuAc=sialyl (N-acetylneuraminyl).

An "acceptor substrate" or an "acceptor saccharide" for a glycosyltransferase, e.g., a CgtD polypeptide, is an oligosaccharide moiety that can act as an acceptor for a particular glycosyltransferase. When the acceptor substrate is contacted with the corresponding glycosyltransferase and sugar donor substrate, and other necessary reaction mixture components, and the reaction mixture is incubated for a sufficient period of time, the glycosyltransferase transfers sugar residues from the sugar donor substrate to the acceptor substrate. The acceptor substrate can vary for different types of a particular glycosyltransferase. Accordingly, the term "acceptor substrate" is taken in context with the particular glycosyltransferase of interest for a particular application. Acceptor substrates for α-1,4-glycosyltransferases, e.g., CgtD from *C. jejuni* LIO87, and additional glycosyltransferases, are described herein. In preferred embodiments, a CgtD acceptor substrate has a terminal galactose residue. CgtD acceptor substrates include, e.g., lactose or lacNAc or oligosaccharides, glycoproteins, glycolipids or glycopeptides that comprise a lactose or lacNAc moiety.

A "donor substrate" for glycosyltransferases is an activated nucleotide sugar. Such activated sugars generally consist of uridine, guanosine, and cytidine monophosphate derivatives of the sugars (UMP, GMP and CMP, respectively) or diphosphate derivatives of the sugars (UDP, GDP and CDP, respectively) in which the nucleoside monophosphate or diphosphate serves as a leaving group. For example, a donor substrate for fucosyltransferases is GDP-fucose. Donor substrates for CgtE proteins include, e.g., UDP-GalNAc or UDP-Gal. Donor substrates for sialyltransferases, for example, are activated sugar nucleotides comprising the desired sialic acid. The donor substrate for CgtD is UDP-Gal. For instance, in the case of NeuAc, the activated sugar is CMP-NeuAc. Bacterial, plant, and fungal systems can sometimes use other activated nucleotide sugars.

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose or furanose.

As used herein, a "galactose moiety" refers to a molecule that includes galactose or that can be derived from galactose. Galactose moieties are usually monosaccharides, e.g., galactose.

As used herein, a "galactosylated product saccharide" refers an oligosaccharide, a polysaccharide, or a carbohydrate moiety, either unconjugated or conjugated to a glycolipid or a glycoprotein, e.g., a biomolecule, that includes a galactose moiety. Any of the above galactose moieties can be used, e.g., galactose. In preferred embodiments the galactose moiety transferred by CgtD is galactose.

In some embodiments other sugar moieties, e.g., fucose, sialic acid, glucose, GalNAc or GlcNAc, are also added to the acceptor substrate through the action of additional glycosyltransferases to produce the galactosylated product saccharide. In some embodiments, the acceptor substrate comprises a galactose moiety and the CgtD protein is used to add an additional galactose moiety, making the galactosylated product saccharide.

The term "sialic acid" or "sialic acid moiety" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al, *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

Much of the nomenclature and general laboratory procedures required in this application can be found in Sambrook, et al., *Molecular Cloning: A Laboratory Manual* (2nd Ed.), Vol. 1-3, Cold Spring Harbor Laboratory, Cold Spring Harbor, N.Y., 1989. The manual is hereinafter referred to as "Sambrook et al."

The terms "CgtD from *C. jejuni* LIO87," "CgtD," or a nucleic acid encoding "CgtD from *C. jejuni* LIO87" or "CgtD" refer to nucleic acids and polypeptide polymorphic variants, alleles, mutants, and interspecies homologs that: (1) have an amino acid sequence that has at least 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to an amino acid sequence encoded by a CgtD from *C. jejuni* LIO87 nucleic acid (for a CgtD from *C. jejuni* LIO87 nucleic acid sequence, see, e.g., SEQ ID NO:1) or to an amino acid sequence of a CgtD from *C. jejuni* LIO87 protein (for a CgtD from *C. jejuni* LIO87 protein sequence, see, e.g., SEQ ID NO:2); (2) bind to antibodies, e.g., polyclonal antibodies, raised against an immunogen comprising an amino acid sequence of a CgtD from *C. jejuni* LIO87 protein, and conservatively modified variants thereof; (3) specifically hybridize under stringent hybridization conditions to an anti-sense strand corresponding to a nucleic acid sequence encoding a CgtD from *C. jejuni* LIO87 protein, and conservatively modified variants thereof; (4) have a nucleic acid sequence that has at least 90%, preferably at least 91%, 92%, 93%, 94%, 95%, 96%, 97%, 98%, 99%, or higher nucleotide sequence identity, preferably over a region of at least about 25, 50, 100, 200, 500, 1000, or more nucleotides, to a CgtD from *C. jejuni* LIO87 nucleic acid, e.g., SEQ ID NO:1, or a nucleic acid encoding the catalytic domain. Preferably the catalytic domain has at least 90%, preferably at least 91%, 92%, 93%, 94%, 95%, 96%, 97%, 98%, 99% amino acid identity to the CgtD from *C. jejuni* LIO87 catalytic domain of SEQ ID NO:2. A polynucleotide or polypeptide sequence is typically from a bacteria including, but not limited to, *Campylobacter, Haemophilus*, and *Pasteurella*. The nucleic acids and proteins of the invention include both naturally occurring or recombinant molecules. A CgtD from *C. jejuni* LIO87 protein typically has α-1,4-galactosyltransferase activity that can be assayed according to methods known to those of skill in the art, using appropriate donor substrates and acceptor substrates, as described herein. Preferred embodiments include a full length CgtD protein of, e.g., SEQ ID NO:2 or a nucleic acid that encodes a full length CgtD protein of, e.g., SEQ ID NO:2.

"Commercial scale" refers to gram scale production of a galactosylated product in a single reaction. In preferred embodiments, commercial scale refers to production of greater than about 50, 75, 80, 90, 100, 125, 150, 175, or 200 grams of galactosylated product.

As used herein, a "truncated CgtD polypeptide" or grammatical variants, refers to a CgtD polypeptide that has been manipulated to remove at least one amino acid residue, relative to a wild type CgtD polypeptide that occurs in nature, so long as the truncated CgtD polypeptide retains enzymatic activity.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

Those of skill recognize that many amino acids can be substituted for one another in a protein without affecting the function of the protein, i.e., a conservative substitution can be the basis of a conservatively modified variant of a protein such as the disclosed CgtD proteins. An incomplete list of conservative amino acid substitutions follows. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V), Alanine (A); 6) Phenylalanine (F), Tyrosine (Y), Tryptophan (W); 7) Serine (S), Threonine (T), Cysteine (C); and 8) Cysteine (C), Methionine (M) (see, e.g., Creighton, Proteins (1984)).

The cells and methods of the invention are useful for producing a galactosylated product, generally by transferring a galactose moiety from a donor substrate to an acceptor molecule. The cells and methods of the invention are also useful for producing a galactosylated product sugar comprising additional sugar residues, generally by transferring a additional monosaccharide or a sulfate groups from a donor substrate to an acceptor molecule. The addition generally takes place at the non-reducing end of an oligosaccharide, polysaccharide (e.g., heparin, carragenin, and the like) or a carbohydrate moiety on a glycolipid or glycoprotein, e.g., a biomolecule. Biomolecules as defined here include but are not limited to biologically significant molecules such as carbohydrates, oligosaccharides, peptides (e.g., glycopeptides), proteins (e.g., glycoproteins), and lipids (e.g., glycolipids, phospholipids, sphingolipids and gangliosides).

The recombinant proteins of the invention can be constructed and expressed as a fusion protein with a molecular "purification tag" at one end, which facilitates purification or identification of the protein. Such tags can also be used for immobilization of a protein of interest during the glycosylation reaction. Suitable tags include "epitope tags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence AspTyrLysAspAspAspAspLys (SEQ ID NO:6) or a substantially identical variant thereof. Other suitable tags are known to those of skill in the art, and include, for example, an affinity tag such as a hexahistidine (SEQ ID NO:7) peptide, which will bind to metal ions such as nickel or cobalt ions or a myc tag. Proteins comprising purification tags can be purified using a binding partner that binds the purification tag, e.g., antibodies to the purification tag, nickel or cobalt ions or resins, and amylose, maltose, or a cyclodextrin. Purification tags also include maltose binding domains and starch binding domains. Purification of maltose binding domain proteins is known to those of skill in the aft. Starch binding domains are described in WO 99/15636, herein incorporated by reference. Affinity purification of a fusion protein comprising a starch binding domain using a betacylodextrin (BCD)-derivatized resin is described in WO 2005/014779, published Feb. 17, 2005, herein incorporated by reference in its entirety.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof. The terms "nucleic acid", "nucleic acid sequence", and "polynucleotide" are used interchangeably herein.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant nucleic acid" refers to a nucleic acid that was artificially constructed (e.g., formed by linking two naturally-occurring or synthetic nucleic acid fragments). This term also applies to nucleic acids that are produced by replication or transcription of a nucleic acid that was artificially constructed. A "recombinant polypeptide" is expressed by transcription of a recombinant nucleic acid (i.e., a nucleic acid that is not native to the cell or that has been modified from its naturally occurring form), followed by translation of the resulting transcript.

A "heterologous polynucleotide" or a "heterologous nucleic acid", as used herein, is one that originates from a source foreign to the particular host cell, or, if from the same source, is modified from its original form. Thus, a heterologous glycosyltransferase gene in a prokaryotic host cell includes a glycosyltransferase gene that is endogenous to the particular host cell but has been modified. Modification of the heterologous sequence may occur, e.g., by treating the DNA with a restriction enzyme to generate a DNA fragment that is capable of being operably linked to a promoter. Techniques such as site-directed mutagenesis are also useful for modifying a heterologous sequence.

A "subsequence" refers to a sequence of nucleic acids or amino acids that comprise a part of a longer sequence of nucleic acids or amino acids (e.g., polypeptide) respectively.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

A "fusion CgtD polypeptide" or a "fusion galactosyltransferase polypeptide" of the invention is a polypeptide that contains a CgtD or an α-1,4-galactosyltransferase catalytic domain. The fusion polypeptide is capable of catalyzing the synthesis of a sugar nucleotide (e.g., UDP-Galactose) as well as the transfer of the sugar residue from the sugar nucleotide to an acceptor molecule. Typically, the catalytic domains of the fusion polypeptides will be at least substantially identical to those of glycosyltransferases and fusion proteins from which the catalytic domains are derived. In some embodiments, a CgtD polypeptide and an epimerase, e.g., UDP-glucose 4' epimerase, polypeptide are fused to form a single polypeptide. For examples of a galactosyltransferase/UDP-glucose 4' epimerase see e.g. WO999/031224, which is herein incorporated by reference for all purposes.

An "accessory enzyme," as referred to herein, is an enzyme that is involved in catalyzing a reaction that, for example, forms a substrate or other reactant for a glycosyltransferase reaction. An accessory enzyme can, for example, catalyze the formation of a nucleotide sugar that is used as a sugar donor moiety by a glycosyltransferase. An accessory enzyme can also be one that is used in the generation of a nucleotide triphosphate that is required for formation of a nucleotide sugar, or in the generation of the sugar which is incorporated into the nucleotide sugar. One example of an accessory enzyme is UDP-glucose 4' epimerase, e.g. GalE from *S. thermophilus* (accession umber M30175)

A "catalytic domain" refers to a portion of an enzyme that is sufficient to catalyze an enzymatic reaction that is normally carried out by the enzyme. For example, a catalytic domain of a CgtD polypeptide will include a sufficient portion of the CgtD to transfer a galactose moiety from a sugar donor to an acceptor saccharide. A catalytic domain can include an entire enzyme, a subsequence thereof, or can include additional amino acid sequences that are not attached to the enzyme or subsequence as found in nature.

The term "isolated" refers to material that is substantially or essentially free from components which interfere with the activity of an enzyme. For cells, saccharides, nucleic acids, and polypeptides of the invention, the term "isolated" refers to material that is substantially or essentially free from components which normally accompany the material as found in its native state. Typically, isolated saccharides, proteins or nucleic acids of the invention are at least about 50%, 55%, 60%, 65%, 70%, 75%, 80% or 85% pure, usually at least about 90%, 91%, 92%, 93%, 94%, 95%, 96%, 97%, 98%, or 99% pure as measured by band intensity on a silver stained gel or other method for determining purity. Purity or homogeneity can be indicated by a number of means well known in the art, such as polyacrylamide gel electrophoresis of a protein or nucleic acid sample, followed by visualization upon staining. For certain purposes high resolution will be needed and HPLC or a similar means for purification utilized. For oligonucleotides, or other galactosylated products, purity can be determined using, e.g., thin layer chromatography, HPLC, or mass spectroscopy.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80% or 85%, most preferably at least 90%, 91%, 92%, 93%, 94%, 95%, 96%, 97%, 98%, or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al, eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mo. Biol.* 215: 403-410 and Altschuel et al. (1977) *Nucleic Acids Res.* 25: 3389-3402, respectively. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na$^+$ ion, typically about 0.01 to 1.0 M Na$^+$ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, N.Y.

The phrases "specifically binds to" or "specifically immunoreactive with", when referring to an antibody refers to a binding reaction which is determinative of the presence of the protein or other antigen in the presence of a heterogeneous population of proteins, saccharides, and other biologics. Thus, under designated immunoassay conditions, the specified antibodies bind preferentially to a particular antigen and do not bind in a significant amount to other molecules present in the sample. Specific binding to an antigen under such conditions requires an antibody that is selected for its specificity for a particular antigen. A variety of immunoassay formats can be used to select antibodies specifically immunoreactive with a particular antigen. For example, solid-phase ELISA immunoassays are routinely used to select monoclonal antibodies specifically immunoreactive with an antigen. See Harlow and Lane (1988) *Antibodies, A Laboratory Manual*, Cold Spring Harbor Publications, New York, for a description of immunoassay formats and conditions that can be used to determine specific immunoreactivity.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. In a preferred embodiment, antibodies that specifically bind to a CgtD protein are produced. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F (ab)'$_2$, a dimer of Fab which itself is a light chain joined to $V_H$-$C_H1$ by a disulfide bond. The F (ab)'$_2$ may be reduced under mild conditions to break the disulfide linkage in the hinge region, thereby converting the F (ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

In one embodiment, the antibody is conjugated to an "effector" moiety. The effector moiety can be any number of molecules, including labeling moieties such as radioactive labels or fluorescent labels for use in diagnostic assays.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to CgtD protein, polymorphic variants, alleles, orthologs, and conservatively modified variants, or splice variants, or portions thereof, can be selected to obtain only those polyclonal antibodies that are specifically immunoreactive with CgtD proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

An "antigen" is a molecule that is recognized and bound by an antibody, e.g., peptides, carbohydrates, organic molecules, or more complex molecules such as glycolipids and glycoproteins. The part of the antigen that is the target of antibody binding is an antigenic determinant and a small functional group that corresponds to a single antigenic determinant is called a hapten.

A "label" is a composition detectable by spectroscopic, photochemical, biochemical, immunochemical, or chemical means. For example, useful labels include $^{32}$P, $^{125}$I, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:2 can be made detectable, e.g., by incorporating a radiolabel into the peptide, and used to detect antibodies specifically reactive with the peptide).

The term "immunoassay" is an assay that uses an antibody to specifically bind an antigen. The immunoassay is characterized by the use of specific binding properties of a particular antibody to isolate, target, and/or quantify the antigen.

The term "carrier molecule" means an immunogenic molecule containing antigenic determinants recognized by T cells. A carrier molecule can be a protein or can be a lipid. A carrier protein is conjugated to a polypeptide to render the polypeptide immunogenic. Carrier proteins include keyhole limpet hemocyanin, horseshoe crab hemocyanin, and bovine serum albumin.

The term "adjuvant" means a substance that nonspecifically enhances the immune response to an antigen. Adjuvants include Freund's adjuvant, either complete or incomplete; Titermax gold adjuvant; alum; and bacterial LPS.

The term "contacting" is used herein interchangeably with the following: combined with, added to, mixed with, passed over, incubated with, flowed over, etc.

III. CgtD Polypeptides

The CgtD polypeptides of the inventions comprise an amino acid sequence that is identical to or shares a specified percent identity with SEQ ID NO:2. The CgtD polypeptide is an α-1,4-galactosyltransferase enzyme and has the functional activity of transferring galactose from UDP-galactose to an oligosaccharide comprising a terminal galactose.

Nucleic acids encoding proteins that are related to the CgtD protein were also identified in other *C. jejuni* strains, e.g., ATCC 43429 and ATC43430. The amino acid sequences of these proteins are found at SEQ ID NO:3 and SEQ ID NO:4. The amino acid sequences of the ATCC 43429 and ATC43430 are identical and share 58% identity with the LIO87 CgtD protein. An alignment of the related proteins is provided in FIG. 2. To date, no activity has been identified for the CgtD polypeptides from ATCC 43429 and ATC43430.

The Clustal W program was used to produce the alignments in FIG. 2. A consensus sequence is included in the figure. Identical, conserved, and semi-conserved amino acid residues are indicated on the figure. Unmarked residues denote regions or residues without apparent conservation.

Using the alignment generated by Clustal W or similar programs known to those of skill, identical, conserved, or semi-conserved residues can be identified and used to predict and avoid changes in amino acid residues that would be detrimental to CgtD activity. Such alignments can also be used to identify amino acid residues that can most likely be changed without affecting protein activity. Amino acid changes, if desired, can be made by selecting a conserved residue as identified herein or on the Clustal W website, or by selecting a modification to one of the corresponding amino acids in a figure such as FIG. 2.

IV. Isolation of Nucleic Acids Encoding CgtD Polypeptides

Nucleic acids that encode CgtD polypeptides include nucleic acids that encode the CgtD polypeptides described above, e.g., SEQ ID NO:2, and conservatively modified variants of that sequence. The CgtD polypeptides of the invention catalyze the transfer of a galactose moiety from a donor substrate to an acceptor substrate.

Nucleic acids that encode additional CgtD polypeptides based on the information disclosed herein, and methods of obtaining such nucleic acids, are known to those of skill in the art. Suitable nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), or the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, Guide to Molecular Cloning Techniques, *Methods in Enzymology* 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

A DNA that encodes a CgtD polypeptide, or a subsequences thereof, can be prepared by any suitable method described above, including, for example, cloning and restriction of appropriate sequences with restriction enzymes. In one preferred embodiment, nucleic acids encoding CgtD polypeptides are isolated by routine cloning methods. A nucleotide sequence of a CgtD polypeptide as provided in, for example, SEQ ID NO: 1, can be used to provide probes that specifically hybridize to a gene encoding a CgtD polypeptide in a genomic DNA sample; or to an mRNA, encoding a CgtD polypeptide comprising, in a total RNA sample (e.g., in a Southern or Northern blot). Once the target nucleic acid encoding a CgtD polypeptide is identified, it can be isolated according to standard methods known to those of skill in the art (see, e.g., Sambrook et al. (1989) *Molecular Cloning: A Laboratory Manual,* 2nd Ed., Vols. 1-3, Cold Spring Harbor Laboratory; Berger and Kimmel (1987) *Methods in Enzymol-* ogy, Vol. 152: Guide to Molecular Cloning Techniques, San Diego: Academic Press, Inc.; or Ausubel et al. (1987) *Current Protocols in Molecular Biology*, Greene Publishing and Wiley-Interscience, New York). Further, the isolated nucleic acids can be cleaved with restriction enzymes to create nucleic acids encoding the full-length CgtD polypeptide, or subsequences thereof, e.g., containing subsequences encoding at least a subsequence of a catalytic domain of the CgtD polypeptide. These restriction enzyme fragments, encoding a CgtD polypeptide or subsequences thereof, may then be ligated, for example, to produce a nucleic acid encoding a CgtD protein.

A nucleic acid encoding a CgtD polypeptide, or a subsequence thereof, can be characterized by assaying for the expressed product. Assays based on the detection of the physical, chemical, or immunological properties of the expressed protein can be used. For example, one can identify a cloned CgtD nucleic acid, by the ability of a protein encoded by the nucleic acid to catalyze the transfer of a galactose moiety from a donor substrate to an acceptor substrate. In one method, capillary electrophoresis is employed to detect the reaction products. This highly sensitive assay involves using either saccharide or disaccharide aminophenyl derivatives which are labeled with fluorescein as described in Wakarchuk et al. (1996) *J. Biol. Chem.* 271 (45): 28271-276. To assay for CgtD activity, Lac-FCHASE can be used as a substrate. The reaction products of other glycosyltransferases can be detected using capillary electrophoresis, e.g., to assay for a *Neisseria* lgtC enzyme, either FCHASE-AP-Lac or FCHASE-AP-Gal can be used, whereas for the *Neisseria* lgtB enzyme an appropriate reagent is FCHASE-AP-GlcNAc (Wakarchuk, supra). To assay for $\alpha$2,8-sialyltransferase, GM3-FCHASE is used as a substrate. See, e.g., U.S. Pat. No. 6,503,744, which is herein incorporated by reference. Other methods for detection of oligosaccharide reaction products include thin layer chromatography and GC/MS and are disclosed in U.S. Pat. No. 6,503,744, which is herein incorporated by reference.

Also, a nucleic acid encoding a CgtD polypeptide, or a subsequence thereof, can be chemically synthesized. Suitable methods include the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.*, 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill recognizes that while chemical synthesis of DNA is often limited to sequences of about 100 bases, longer sequences may be obtained by the ligation of shorter sequences.

Nucleic acids encoding CgtD polypeptides, or subsequences thereof, can be cloned using DNA amplification methods such as polymerase chain reaction (PCR). Thus, for example, the nucleic acid sequence or subsequence is PCR amplified, using a sense primer containing one restriction enzyme site (e.g., NdeI) and an antisense primer containing another restriction enzyme site (e.g., HindIII). This will produce a nucleic acid encoding the desired CgtD polypeptide or a subsequence and having terminal restriction enzyme sites. This nucleic acid can then be easily ligated into a vector containing a nucleic acid encoding the second molecule and having the appropriate corresponding restriction enzyme sites. Suitable PCR primers can be determined by one of skill in the art using the sequence information provided in Gen-Bank or other sources. Appropriate restriction enzyme sites can also be added to the nucleic acid encoding the CgtD protein or a protein subsequence thereof by site-directed mutagenesis. The plasmid containing the CgtD protein-encoding nucleotide sequence or subsequence is cleaved with the appropriate restriction endonuclease and then ligated into an appropriate vector for amplification and/or expression according to standard methods. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

Some nucleic acids encoding bacterial CgtD proteins can be amplified using PCR primers based on the sequence of CgtD nucleic acids disclosed herein. Examples of PCR primers that can be used to amplify nucleic acid that encode CgtD proteins include the following primer pairs:

```
CJ-636 Primer
                                      (SEQ ID NO: 8)
TAAAAGGCTACATATGACTGAAATTTCAAGTTTTTGG
(NdeI site is underlined)

CJ-639 Primer
                                      (SEQ ID NO: 9)
GGCAAGATGATTGTCGACTTAGGCATTGTTTTTC
(SalI site is underlined)
```

In some bacteria, nucleic acids encoding CgtD protein can be isolated by amplifying a specific chromosomal locus, e.g., the LOS locus of *C. jejuni*, and then identifying a CgtD nucleic acid typically found at that locus (see, e.g., U.S. Pat. No. 6,503,744). Examples of PCR primers that can be used to amplify an LOS locus comprising nucleic acids encoding a CgtD protein include the following primer pairs:

```
CJ42:
Primer in heptosylTase-II
                                     (SEQ ID NO: 10)
5' GC CAT TAC CGT ATC GCC TAA CCA GG 3' 25 mer CJ43:
Primer in heptosylTase-I
                                     (SEQ ID NO: 11)
5' AAA GAA TAC GAA TTT GCT AAA GAG G 3' 25 mer
```

Other physical properties of a recombinant CgtD polypeptide expressed from a particular nucleic acid, can be compared to properties of known CgtD polypeptides to provide another method of identifying suitable sequences or domains of the CgtD polypeptide that are determinants of acceptor substrate specificity and/or catalytic activity. Alternatively, a putative CgtD polypeptide or recombinant CgtD polypeptide can be mutated, and its role as a glycosyltransferase, or the role of particular sequences or domains established by detecting a variation in the structure of a carbohydrate normally produced by the non-mutated, naturally-occurring, or control CgtD polypeptide. Those of skill will recognize that mutation or modification of CgtD polypeptides of the invention can be facilitated by molecular biology techniques to manipulate the nucleic acids encoding the CgtD polypeptides, e.g., PCR.

Functional domains of newly identified CgtD polypeptides can be identified by using standard methods for mutating or modifying the polypeptides and testing them for activities such as acceptor substrate activity and/or catalytic activity, as described herein. The functional domains of the various CgtD polypeptides can be used to construct nucleic acids encoding CgtD polypeptides and the functional domains of one or more CgtD polypeptides. These multi-CgtD fusion proteins can then be tested for the desired acceptor substrate or catalytic activity.

In an exemplary approach to cloning nucleic acids encoding CgtD proteins, the known nucleic acid or amino acid sequences of cloned CgtD polypeptides are aligned and compared to determine the amount of sequence identity between various CgtD polypeptides. This information can be used to identify and select protein domains that confer or modulate CgtD activities, e.g., acceptor substrate activity and/or catalytic activity based on the amount of sequence identity between the CgtD proteins of interest. For example, domains having sequence identity between the CgtD proteins of interest, and that are associated with a known activity, can be used to construct CgtD proteins containing that domain, and having the activity associated with that domain (e.g., acceptor substrate specificity and/or catalytic activity).

V. Expression of CgtD Polypeptides in Host Cells

CgtD proteins of the invention can be expressed in a variety of host cells, including *E. coli*, other bacterial hosts, and yeast. The host cells are preferably microorganisms, such as, for example, yeast cells, bacterial cells, or filamentous fungal cells. Examples of suitable host cells include, for example, *Azotobacter* sp. (e.g., *A. vinelandii*), *Pseudomonas* sp., *Rhizobium* sp., *Erwinia* sp., *Escherichia* sp. (e.g., *E. coli*), *Bacillus, Pseudomonas, Proteus, Salmonella, Serratia, Shigella, Rhizobia, Vitreoscilla, Paracoccus* and *Klebsiella* sp., among many others. The cells can be of any of several genera, including *Saccharomyces* (e.g., *S. cerevisiae*), *Candida* (e.g., *C. utilis, C. parapsilosis, C. krusei, C. versatilis, C. lipolytica, C. zeylanoides, C. guilliermondii, C. albicans*, and *C. humicola*), *Pichia* (e.g., *P. farinosa* and *P. ohmeri*), *Torulopsis* (e.g., *T. candida, T. sphaerica, T. xylinus, T famata*, and *T. versatilis*), Debaryomyces (e.g., *D. subglobosus, D. cantarellii, D. globosus, D. hansenii*, and *D. japonicus*), Zygosaccharomyces (e.g., *Z. rouxii* and *Z. bailii*), Kluyveromyces (e.g., *K. marxianus*), Hansenula (e.g., *H. anomala* and *H. jadinii*), and Brettanomyces (e.g., *B. lambicus* and *B. anomalus*). Examples of useful bacteria include, but are not limited to, *Escherichia, Enterobacter, Azotobacter, Erwinia, Klebsielia, Bacillus, Pseudomonas, Proteus*, and *Salmonella*.

Once expressed in a host cell, the CgtD polypeptides can be used to produced galactosylated products. For example, the CgtD polypeptides can be isolated using standard protein purification techniques and used in in vitro reactions described herein to make galactosylated products. Partially purified CgtD polypeptides can also be used in in vitro reactions to make galactosylated products as can the permeabilized host cells. The host cells can also be used in an in vivo system (e.g., fermentative production) to produce galactosylated products.

Typically, the polynucleotide that encodes the CgtD polypeptides is placed under the control of a promoter that is functional in the desired host cell. An extremely wide variety of promoters are well known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the invention provides expression cassettes into which the nucleic acids that encode fusion proteins are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

For expression of CgtD proteins in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli*.

A ribosome binding site (RBS) is conveniently included in the expression cassettes of the invention. An RBS in *E. coli*, for example, consists of a nucleotide sequence 3-9 nucleotides in length located 3-11 nucleotides upstream of the initiation codon (Shine and Dalgarno, *Nature* (1975) 254: 34; Steitz, In *Biological regulation and development: Gene expression* (ed. R. F. Goldberger), vol. 1, p. 349, 1979, Plenum Publishing, NY).

For expression of the CgtD proteins in yeast, convenient promoters include GAL1-(Johnson and Davies (1984) *Mol. Cell. Biol.* 4:1440-1448) ADH2 (Russell et al. (1983) *J. Biol. Chem.* 258:2674-2682), PHO5 (*EMBO J.* (1982) 6:675-680), and MFac (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181-209). Another suitable promoter for use in yeast is the ADH2/GAPDH hybrid promoter as described in Cousens et al., *Gene* 61:265-275 (1987). For filamentous fungi such as, for example, strains of the fungi *Aspergillus* (McKnight et al., U.S. Pat. No. 4,935,349), examples of useful promoters include those derived from *Aspergillus nidulans* glycolytic genes, such as the ADH3 promoter (McKnight et al., *EMBO J.* 4: 2093 2099 (1985)) and the tpiA promoter. An example of a suitable terminator is the ADH3 terminator (McKnight et al.).

Either constitutive or regulated promoters can be used in the present invention. Regulated promoters can be advantageous because the host cells can be grown to high densities before expression of the fusion proteins is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the glycosyltransferase or enzyme involved in nucleotide sugar synthesis. For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82: 1074-8). These promoters and their use are discussed in Sambrook et al., supra. A particularly preferred inducible promoter for expression in prokaryotes is a dual promoter that includes a tac promoter component linked to a promoter component obtained from a gene or genes that encode enzymes involved in galactose metabolism (e.g., a promoter from a UDP galactose 4-epimerase gene (galE)). The dual tac-gal promote is described in PCT Patent Application Publ. No. WO98/20111.

A construct that includes a polynucleotide of interest operably linked to gene expression control signals that, when placed in an appropriate host cell, drive expression of the polynucleotide is termed an "expression cassette." Expression cassettes that encode the fusion proteins of the invention are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria. Alternatively, the vector can replicate by becoming integrated into the host cell genomic complement and being replicated as the cell undergoes DNA replication. A preferred expression vector for expression of the enzymes is in bacterial cells is pTGK, which includes a dual tac-gal promoter and is described in PCT Patent Application Publ. NO. WO98/20111.

The construction of polynucleotide constructs generally requires the use of vectors able to replicate in bacteria. A plethora of kits are commercially available for the purification of plasmids from bacteria (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to express the polynucleotides of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. Often, the vector will have one selectable marker that is functional in, e.g., *E. coli*, or other cells in which the vector is replicated prior to being introduced into the host cell. A number of selectable markers are known to those of skill in the art and are described for instance in Sambrook et al., supra.

Construction of suitable vectors containing one or more of the above listed components employs standard ligation techniques as described in the references cited above. Isolated plasmids or DNA fragments are cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

A variety of common vectors suitable for use as starting materials for constructing the expression vectors of the invention are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses).

The methods for introducing the expression vectors into a chosen host cell are not particularly critical, and such methods are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The CgtD polypeptides can be expressed intracellularly, or can be secreted from the cell. Intracellular expression often results in high yields. If necessary, the amount of soluble, active fusion protein may be increased by performing refolding procedures (see, e.g., Sambrook et al., supra.; Marston et al., *Bio/Technology* (1984) 2: 800; Schoner et al., *Bio/Technology* (1985) 3: 151). In embodiments in which the CgtD polypeptides are secreted from the cell, either into the periplasm or into the extracellular medium, the DNA sequence is linked to a cleavable signal peptide sequence. The signal sequence directs translocation of the fusion protein through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc.*

Natl. Acad. Sci. USA (1985) 82: 7212; Talmadge et al., *Proc. Natl. Acad. Sci. USA* (1980) 77: 3988; Takahara et al., *J. Biol. Chem.* (1985) 260: 2670). In another embodiment, the CgtD proteins are fused to a subsequence of protein A or bovine serum albumin (BSA), for example, to facilitate purification, secretion, or stability.

The CgtD polypeptides of the invention can also be further linked to other bacterial proteins. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook et al., supra.). For certain applications, it may be desirable to cleave the non-glycosyltransferase and/or accessory enzyme amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

More than one recombinant protein may be expressed in a single host cell by placing multiple transcriptional cassettes in a single expression vector, or by utilizing different selectable markers for each of the expression vectors which are employed in the cloning strategy.

A suitable system for obtaining recombinant proteins from *E. coli* which maintains the integrity of their N-termini has been described by Miller et al. *Biotechnology* 7:698-704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

VI. Purification of CgtD Polypeptides

The CgtD proteins of the present invention can be expressed, e.g., as intracellular proteins or as proteins that are secreted from the cell, and can be used in this form, in the methods of the present invention. For example, a crude cellular extract containing the expressed intracellular or secreted CgtD polypeptide can used in the methods of the present invention.

Alternatively, the CgtD polypeptide can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification*, Academic Press, Inc. N.Y. (1990)). Substantially pure compositions of at least about 70, 75, 80, 85, 90% homogeneity are preferred, and 92, 95, 98 to 99% or more homogeneity are most preferred. The purified proteins may also be used, e.g., as immunogens for antibody production.

To facilitate purification of the CgtD polypeptides of the invention, the nucleic acids that encode the proteins can also include a coding sequence for an epitope or "tag" for which an affinity binding reagent is available, i.e. a purification tag. Examples of suitable epitopes include the myc and V-5 reporter genes; expression vectors useful for recombinant production of fusion proteins having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the CgtD polypeptide of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines (SEQ ID NO:7) are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)). Other purification or epitope tags include, e.g., AU1, AU5, DDDDK (SEQ ID NO:12) (EC5), E tag, E2 tag, Glu-Glu, a 6 residue peptide, EYMPME (SEQ ID NO: 13), derived from the Polyoma middle T protein, HA, HSV, IRS, KT3, S tage, Si tag, T7 tag, V5 tag, VSV-G, β-galactosidase, Gal4, green fluorescent protein (GFP), luciferase, protein C, protein A, cellulose binding protein, GST (glutathione S-transferase), a step-tag, Nus-S, PPI-ases, Pfg 27, calmodulin binding protein, dsb A and fragments thereof, and granzyme B. Epitope peptides and antibodies that bind specifically to epitope sequences are commercially available from, e.g., Covance Research Products, Inc.; Bethyl Laboratories, Inc.; Abcam Ltd.; and Novus Biologicals, Inc.

Purification tags also include maltose binding domains and starch binding domains. Proteins comprising purification tags can be purified using a binding partner that binds the purification tag, e.g., antibodies to the purification tag, nickel or cobalt ions or resins, and amylose, maltose, or a cyclodextrin. Purification tags also include starch binding domains, *E. coli* thioredoxin domains (vectors and antibodies commercially available from e.g., Santa Cruz Biotechnology, Inc. and Alpha Diagnostic International, Inc.), and the carboxy-terminal half of the SUMO protein (vectors and antibodies commercially available from e.g., Life Sensors Inc.). Starch binding domains, such as a maltose binding domain from *E. coli* and SBD (starch binding domain) from an amylase of *A. niger*, are described in WO 99/15636, herein incorporated by reference. Affinity purification of a fusion protein comprising a starch binding domain using a betacyclodextrin (BCD)-derivatized resin is described in WO 2005/014779, published Feb. 17, 2005, herein incorporated by reference in its entirety. In some embodiments, a CgtD polypeptide comprises more than one purification or epitope tag.

Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that modifications can be made to the catalytic or functional domains of the CgtD polypeptide without diminishing their biological activity. Some modifications may be made to facilitate the cloning, expression, or incorporation of the catalytic domain into a fusion protein. Such modifications are well known to those of skill in the art and include, for example, the addition of codons at either terminus of the polynucleotide that encodes the catalytic domain to provide, for example, a methionine added at the amino terminus to provide an initiation site, or additional amino acids (e.g., poly H is) placed on either terminus to create conveniently located restriction enzyme sites or termination codons or purification sequences.

VII. Fusion CgtD Proteins

In some embodiments, the recombinant cells of the invention express fusion proteins that have more than one enzymatic activity that is involved in synthesis of a desired galactosylated oligosaccharide. The fusion polypeptides can be composed of, for example, a CgtD polypeptide that is joined to a an accessory enzyme, e.g., [UDP-GalNAc 4' epimerase or a UDP-glucose 4' epimerase. Fusion proteins can also be made using catalytic domains or other truncations of the enzymes. For example, a polynucleotide that encodes a CgtD polypeptide can be joined, in-frame, to a polynucleotide that encodes, e.g., a UDP-GalNAc 4' epimerase or a UDP-glucose 4' epimerase. The resulting fusion protein can then catalyze not only the synthesis of the activated galactose molecule, but also the transfer of the galactose moiety to the acceptor molecule. The fusion protein can be two or more galactose cycle enzymes linked into one expressible nucleotide sequence. The fusion CgtD polypeptides of the present invention can be readily designed and manufactured utilizing various recombinant DNA techniques well known to those skilled in the art. Exemplary fusion proteins are described in PCT Patent Application PCT/CA98/01180, which was published as WO99/31224 on Jun. 24, 1999 and which discloses CMP-sialic acid synthase from Neisseria fused with an α2,3-sialyltransferase from Neisseria. In some embodiments, more that one fusion CgtD polypeptide is expressed in the cell. Fusion protein can also comprise purification or epitope tags as described herein.

VIII. Donor Substrates and Acceptor Substrates

Suitable donor substrates used by the CgtD polypeptides include e.g., UDP-Gal. Guo et al., *Applied Biochem. and Biotech.* 68: 1-20 (1997).

Typically, acceptor substrates include a terminal lactose or LacNAc derivatives for addition of a galactose residue by an α1,4 linkage. Examples of suitable acceptors include a terminal Gal that is linked to GlcNAc or Glc by a β1,4 linkage, and a terminal Gal that is β1,3-linked to either GlcNAc or GalNAc. Suitable acceptors, include, for example, lactose and LacNAc, and other acceptors that can be determined by those of skill in the art. The terminal residue to which the galactose moiety is attached can itself be attached to, for example, H, a saccharide, oligosaccharide, or an aglycone group having at least one carbohydrate atom. In some embodiments, the acceptor residue is a portion of an oligosaccharide that is attached to a peptide, a protein, a lipid, or a proteoglycan, for example.

Suitable acceptor substrates used by the CgtD polypeptides and methods of the invention include, but are not limited to, polysaccharides and oligosaccharides. The CgtD polypeptides described herein can also be used in multienzyme systems to produce a desired product from a convenient starting material.

Suitable acceptor substrates used by the CgtD polypeptides and methods of the invention include, but are not limited to, proteins, lipids, peptides, glycoproteins, glycolipids, glycopeptides, gangliosides and other biological structures (e.g., whole cells) that can be modified by the methods of the invention. These acceptor substrates will typically comprise the polysaccharide or oligosaccharide molecules described above. Exemplary structures, which can be modified by the methods of the invention include any a of a number glycolipids, glycoproteins and carbohydrate structures on cells known to those skilled in the art.

The present invention provides CgtD polypeptides that are selected for their ability to produce oligosaccharides, glycoproteins and glycolipids having desired oligosaccharide moieties. Similarly, if present, accessory enzymes are chosen based on an desired activated sugar substrate or on a sugar found on the product oligosaccharide.

For synthesis of glycoproteins, one can readily identify suitable CgtD polypeptides by reacting various amounts of a CgtD polypeptide of interest (e.g., 0.01-100 mU/mg protein) with a glycoprotein (e.g., at 1-10 mg/ml) to which is linked an oligosaccharide that has a potential acceptor site for glycosylation by the CgtD protein of interest. The abilities of the recombinant CgtD proteins of the present invention to add a sugar residue at the desired acceptor site are compared, and a CgtD polypeptide having the desired property (e.g., acceptor substrate specificity or catalytic activity) is selected.

In general, the efficacy of the enzymatic synthesis of oligosaccharides, glycoproteins, and glycolipids, having desired galactosylated oligosaccharide moieties, can be enhanced through use of recombinantly produced CgtD polypeptides of the present invention. Recombinant techniques enable production of the recombinant CgtD polypeptides in the large amounts that are required for large-scale in vitro oligosaccharide, glycoprotein and glycolipid modification.

In some embodiments, suitable oligosaccharides, glycoproteins, and glycolipids for use by the CgtD polypeptides and methods of the invention can be glycoproteins and glycolipids immobilized on a solid support during the glycosylation reaction. The term "solid support" also encompasses semi-solid supports. Preferably, the target glycoprotein or glycolipid is reversibly immobilized so that the respective glycoprotein or glycolipid can be released after the glycosylation reaction is completed. Many suitable matrices are known to those of skill in the art. Ion exchange, for example, can be employed to temporarily immobilize a glycoprotein or glycolipid on an appropriate resin while the glycosylation reaction proceeds. A ligand that specifically binds to the glycoprotein or glycolipid of interest can also be used for affinity-based immobilization. For example, antibodies that specifically bind to a glycoprotein are suitable. Also, where the glycoprotein of interest is itself an antibody or contains a fragment thereof, one can use protein A or G as the affinity resin. Dyes and other molecules that specifically bind to a glycoprotein or glycolipid of interest are also suitable.

Preferably, when the acceptor saccharide is a truncated version of the full-length glycoprotein, it preferably includes the biologically active subsequence of the full-length glycoprotein. Exemplary biologically active subsequences include, but are not limited to, enzyme active sites, receptor binding sites, ligand binding sites, complementarity determining regions of antibodies, and antigenic regions of antigens.

Ix. Production of Galactosylated Products

CgtD polypeptides can be used to make galactosylated products in in vitro reactions mixes or by in vivo reactions, e.g., by fermentative growth of recombinant microorganisms that comprise nucleotides that encode CgtD polypeptides.

A. In vitro Reactions

The CgtD polypeptides can be used to make galactosylated products in in vitro reactions mixes. The in vitro reaction mixtures can include permeabilized microorganisms comprising the CgtD polypeptides, partially purified CgtD polypeptides, or purified CgtD polypeptides; as well as donor substrates acceptor substrates, and appropriate reaction buffers. For in vitro reactions, the recombinant glycosyltransferase proteins, such as CgtD polypeptides, acceptor substrates, donor substrates and other reaction mixture ingredients are combined by admixture in an aqueous reaction medium. Additional glycosyltransferases can be used in combination with the CgtD polypeptides, depending on the desired galactosylated product. The medium generally has a pH value of about 5 to about 8.5. The selection of a medium is based on the ability of the medium to maintain pH value at the desired level. Thus, in some embodiments, the medium is buffered to a pH value of about 7.5. If a buffer is not used, the pH of the medium should be maintained at about 5 to 8.5, depending upon the particular glalactosyltransferase used. For CgtD polypeptides, the pH range is preferably maintained from about 7.0 to 8.0. For sialyltransferases, the range is preferably from about 5.5 to about 8.0.

Enzyme amounts or concentrations are expressed in activity units, which is a measure of the initial rate of catalysis. One activity unit catalyzes the formation of 1 μmol of product per minute at a given temperature (typically 37° C.) and pH value (typically 7.5). Thus, 10 units of an enzyme is a catalytic amount of that enzyme where 10 μmol of substrate are converted to 10 μmol of product in one minute at a temperature of 37° C. and a pH value of 7.5.

The reaction mixture may include divalent metal cations ($Mg^{2+}$, $Mn^{2+}$). The reaction medium may also comprise solubilizing detergents (e.g., Triton or SDS) and organic solvents such as methanol or ethanol, if necessary. The enzymes can be utilized free in solution or can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about 0° C. to about 45° C., and more preferably at about 20° C. to about 37° C.

The reaction mixture so formed is maintained for a period of time sufficient to obtain the desired high yield of desired oligosaccharide determinants present on oligosaccharide groups attached to the biomolecule to be glycosylated. For large-scale preparations, the reaction will often be allowed to proceed for between about 0.5-240 hours, and more typically between about 1-36 hours.

One or more of the glycosyltransferase reactions can be carried out as part of a glycosyltransferase cycle. Preferred conditions and descriptions of glycosyltransferase cycles have been described. A number of glycosyltransferase cycles (for example, sialyltransferase cycles, galactosyltransferase cycles, and fucosyltransferase cycles) are described in U.S. Pat. No. 5,374,541 and WO 9425615 A. Other glycosyltransferase cycles are described in Ichikawa et al. *J. Am. Chem. Soc.* 114:9283 (1992), Wong et al. *J. Org. Chem.* 57: 4343 (1992), DeLuca, et al, *J. Am. Chem. Soc.* 117:5869-5870 (1995), and Ichikawa et al. *In Carbohydrates and Carbohydrate Polymers*. Yaltami, ed. (ATL Press, 1993).

For the above glycosyltransferase cycles, the concentrations or amounts of the various reactants used in the processes depend upon numerous factors including reaction conditions such as temperature and pH value, and the choice and amount of acceptor saccharides to be glycosylated. Because the glycosylation process permits regeneration of activating nucleotides, activated donor sugars and scavenging of produced PPi in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants.

Preferably, the concentrations of activating nucleotides, phosphate donor, the donor sugar and enzymes are selected such that glycosylation proceeds until the acceptor is consumed. The considerations discussed below, while in the context of a sialyltransferase, are generally applicable to other glycosyltransferase cycles.

Each of the enzymes is present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

B. In vivo Reactions

The CgtD polypeptides can be used to make galactosylated products by in vivo reactions, e.g., fermentative growth of recombinant microorganisms comprising the CgtD polypeptides. Fermentative growth of recombinant microorganisms can occur in the presence of medium that includes an acceptor substrate, e.g. lactose or LacNAc and a donor substrate or a precursor to a donor substrate, e.g., galactose. See, e.g., Priem et al., *Glycobiology* 12:235-240 (2002). The microorganism takes up the acceptor substrate and the donor substrate or the precursor to a donor substrate and the addition of the donor substrate to the acceptor substrate takes place in the living cell. The microorganism can be altered to facilitate uptake of the acceptor substrate, e.g., by expressing a sugar transport protein. For example, where lactose is the acceptor saccharide, *E. coli* cells that express the LacY permease can be used. Other methods can be used to decrease breakdown of an acceptor saccharide or to increase production of a donor saccharide or a precursor of the donor saccharide. In some embodiments, production of galactosylated products is enhanced by manipulation of the host microorganism. For example, in *E. coli*, break down of sialic acid can be minimized by using a host strain that is lacking, e.g., CMP-sialate synthase (NanA-). (In some strains of *E. coli*, CMP-sialate synthase appears to be a catabolic enzyme.) Also in *E. coli*, when lactose is, for example, the acceptor saccharide or an intermediate in synthesizing the galactosylated product, lactose breakdown can be minimized by using host cells that are LacZ-.

C. Characterization of and Isolation of Galactosylated Products

The production of galactosylated products can be monitored by e.g., determining that production of the desired product has occurred or by determining that a substrate such as the acceptor substrate has been depleted. Those of skill will recognize that galactosylated products such as oligosaccharide, can be identified using techniques such as chromatography, e.g., using paper or TLC plates, or by mass spectrometry, e.g., MALDI-TOF spectrometry, or by NMR spectroscopy. Methods of identification of galactosylated products are known to those of skill in the art and are found, e.g., in U.S. Pat. No. 6,699,705, which is herein incorporated by reference for all purposes and in Varki et al., *Preparation and Analysis of Glycoconjugates*, in Current Protocols in Molecular Biology, Chapter 17 (Ausubel et al. eds, 1993).

The products produced using CgtD polypeptides can be used without purification. However, standard, well known techniques, for example, thin or thick layer chromatography, ion exchange chromatography, or membrane filtration can be used for recovery of galactosylated saccharides. Also, for example, membrane filtration, utilizing a nanofiltration or reverse osmotic membrane as described in commonly assigned AU Patent No. 735695 may be used. As a further example, membrane filtration wherein the membranes have a molecular weight cutoff of about 1000 to about 10,000 Daltons can be used to remove proteins. As another example, nanofiltration or reverse osmosis can then be used to remove salts. Nanofilter membranes are a class of reverse osmosis membranes which pass monovalent salts but retain polyvalent salts and uncharged solutes larger than about 200 to about 1000 Daltons, depending upon the membrane used. Thus, for example, the oligosaccharides produced by the compositions and methods of the present invention can be retained in the membrane and contaminating salts will pass through. Glycoprotein galactosylated products can be isolated or purified using standard protein purification techniques, including those described herein.

It must be noted that as used herein and in the appended claims, the singular forms "a", "and", and "the" include plural referents unless the context clearly dictates otherwise. Thus, for example, reference to "a nucleic acid" includes a plurality of such nucleic acids and reference to "the polypeptide" includes reference to one or more polypeptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All citations are incorporated herein by reference.

EXAMPLES

Example 1

Cloning, Expression and Characterization of CgtD from *C. jejuni* LIO87

ORF #8 from *C. jejuni* LIO87 (SEQ ID NO:1) was cloned and expressed in *Escherichia coli*. The extracts from *Escherichia coli* that overexpress the protein of SEQ ID NO:2 were assayed with UDP-Glc, UDP-GlcNAc, UDP-Gal and UDP-GalNAc as donors and the fluorescent derivatives of Glc, Gal, Lac, LacNAc and Gal-α-1,4-Lac as acceptors. The protein product of ORF #8 (SEQ ID NO:2) was active with UDP-Gal as donor and either the LacNAc (Gal-β-1,4-GlcNAc) or the Lac (Gal-β-1,4-Glc) derivatives as acceptor. SEQ ID NO:2 was designated CgtD (Campylobacter glycosyltransferase; D) and further characterized.

Example 2

Further Characterization of CgtD Activity

To further characterize the enzymatic activity of CgtD, the gene encoding CgtD from *C. jejuni* LIO87 was cloned in pCWori+ as a C-terminal fusion with the *E. coli* maltose-binding (MalE) protein (construct CJL-99). CJL-99 was electroporated in *E. coli* AD202. CgtD expressed well as a MalE fusion (about 150 units per liter). The activity was assessed on the donors and acceptors determined optimal in Example I. Activity was optimal at pH 7 to 8. Inclusion of divalent cations increased activity. Some divalent cations were more beneficial than others e.g., $MnCl_2$ yielded about 15% better activity than $MgCl_2$.

Example 3

Determining the Regio- and Stereo-Specificity of CgtD

The regio- and stereo-specificity of CgtD were determined using purified MalE-CgtD (CJL-99). 19 mg of αGal-1,4-βGal-1,4-βGlcNAc-p-nitrophenyl were synthesized. The $^1$H NMR resonances were assigned to the trisaccharide compound through the use of 2D homonuclear COSY and TOCSY spectra as shown in FIG. 1. These assignments were used to identify cross-peaks in an $^1$H-$^{13}$C HSQC spectrum, which correlates the chemical shift of a proton atom with its directly bonded carbon neighbor (FIG. 2). Because inter-residue connectivities can be established across glycosidic bonds using a $^1$H-$^{13}$C HMBC pulse sequence, HMBC spectra of the trisaccharide compound were acquired to establish the covalent linkages between sugar residues. These data confirmed that CgtD transferred a Gal residue to a Gal on the disaccharide precursor through an α1→4 linkage. Consistent with the HMBC spectra, the carbon resonance at position C4 of βGal displayed a downfiled shift in comparison with monosaccharide values. This shift is a qualitative indicator of a glycosidic linkage with the adjacent βGal residue.

Example 4

BLAST Sequence Searches for CgtD Homologues

A BLASTP search using CgtD from *C. jejuni* LIO87 (SEQ ID NO:2) did not reveal any significant homologue from organisms other than *C. jejuni*. Two *C. jejuni* strains (ATCC 43429 and ATC43430) have homologues of CgtD (SEQ ID NO:3 and SEQ ID NO:4) that are identical between themselves and share 58% identity with CgtD from *C. jejuni* LIO87 (FIG. 3). To date, no activity has been identified for the CgtD polypeptides from ATCC 43429 and ATC43430.

The Clustal W program was used to produce the alignments in FIG. 3. The following symbols are used: "*" all sequences in the alignment have identical e residues; ":" conserved substitutions are present; and "." semi-conserved substitutions are present. See, e.g., www.ebi.ac.uk/clustalw/#. The website defines conserved substitutions by designating amino acids in the following groups as interchangeable: A, V, F, P, M, I, L and W; D and E; R, H and K; and S, T, Y, H, C, N, G and Q. The bottom sequence is a consensus sequence generated by the program.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A method of producing a galactosylated product saccharide, the method comprising the step of:
   a) contacting an acceptor substrate with a reaction mixture comprising an isolated or recombinant α-1,4-galactosyltransferase polypeptide, at least one divalent metal cation and a donor substrate comprising a galactose moiety, wherein the α-1,4-galactosyltransferase polypeptide comprises an amino acid sequence with at least 90% identity to SEQ ID NO:2; and
   b) allowing transfer of the galactose moiety to the acceptor substrate to occur, thereby producing the galactosylated product saccharide.

2. The method of claim 1, wherein the α-1,4-galactosyltransferase polypeptide comprises an amino acid sequence with at least 95% identity to SEQ ID NO:2.

3. The method of claim 1, wherein the α-1,4-galactosyltransferase polypeptide comprises an amino acid sequence of SEQ ID NO:2.

4. The method of claim 1, wherein the method is performed at a commercial scale of production.

5. The method of claim 1, wherein the reaction mixture has a pH from 5.5 to 8.0.

\* \* \* \* \*

SEQUENCE LISTING

<160> NUMBER OF SEQ ID NOS: 13

<210> SEQ ID NO 1
<211> LENGTH: 888
<212> TYPE: DNA

<213> ORGANISM: Campylobacter jejuni
<220> FEATURE:
<223> OTHER INFORMATION: Campylobacter jejuni LIO87
      alpha-1,4-galactosyltransferase (Campylobacter
      glycosyltransferase D, CgtD) ORF #8

<400> SEQUENCE: 1

```
atgactgaaa tttcaagttt ttggtatact cctaaaggct ataagggtat aggtttaatg      60
gaaattctta cgattaaatc ttggcttgat catgggtata aattccatct atatacttat     120
aatttagaag ataaaatttt tttaaaattc caagagctgt ttgataattt tatacttaaa     180
gatgcaaatg aaatcatacc ttttgaagaa tattttagcg atgatagggg agctggagta     240
gctgctttt cagattttt taggtttaat ctactttatc tcaggggggg ggtatgggtg      300
gatcttgata tggtgtgttt aaaccattat gattatgata aaaagaata tatttttct      360
aaggaaattg ataatgatct aagcaaagct agaatcacaa cttcactcct taaatttcca     420
aaacaaagtg aatttggaaa attaattata gatgaagcaa aaaagattgt tgatgataac     480
aaaataattc cttggggtat tataggtcct tggttttag ctaaatgggt taagaatat       540
gatttagaaa acatgctctc tagactataaa gatacttgtc aaatttcttg tggtaatact    600
agagattta tagataaaaa aatttttcgat aaaaacagac tttgtttgca tttatttct     660
gaaatgtgga aaatttataa aatgaataaa atcattttt ataaatcatg catttatgga     720
ttttacttc aaaagcacaa atccttgat ttatgtctta aattaaatta taatcttagt      780
ttttgcgata acattatga taaattcctt ccttttatta atataaaaaa taaaataaga     840
ttttattttc gccacccaaa aaagattttt aagaaaaaca atgcctaa               888
```

<210> SEQ ID NO 2
<211> LENGTH: 295
<212> TYPE: PRT
<213> ORGANISM: Campylobacter jejuni
<220> FEATURE:
<223> OTHER INFORMATION: Campylobacter jejuni LIO87
      alpha-1,4-galactosyltransferase (Campylobacter
      glycosyltransferase D, CgtD) ORF #8

<400> SEQUENCE: 2

```
Met Thr Glu Ile Ser Ser Phe Trp Tyr Thr Pro Lys Gly Tyr Lys Gly
  1               5                  10                  15

Ile Gly Leu Met Glu Ile Leu Thr Ile Lys Ser Trp Leu Asp His Gly
             20                  25                  30

Tyr Lys Phe His Leu Tyr Thr Tyr Asn Leu Glu Asp Lys Ile Phe Leu
         35                  40                  45

Lys Phe Gln Glu Leu Phe Asp Asn Phe Ile Leu Lys Asp Ala Asn Glu
     50                  55                  60

Ile Ile Pro Phe Glu Glu Tyr Phe Ser Asp Asp Arg Gly Ala Gly Val
 65                  70                  75                  80

Ala Ala Phe Ser Asp Phe Phe Arg Phe Asn Leu Tyr Leu Arg Gly
             85                  90                  95

Gly Val Trp Val Asp Leu Asp Met Val Cys Leu Asn His Tyr Asp Tyr
            100                 105                 110

Asp Lys Lys Glu Tyr Ile Phe Ser Lys Glu Ile Asp Asn Asp Leu Ser
        115                 120                 125

Lys Ala Arg Ile Thr Thr Ser Leu Leu Lys Phe Pro Lys Gln Ser Glu
    130                 135                 140

Phe Gly Lys Leu Ile Ile Asp Glu Ala Lys Lys Ile Val Asp Asp Asn
145                 150                 155                 160
```

```
Lys Ile Ile Pro Trp Gly Ile Gly Pro Trp Phe Leu Ala Lys Trp
            165                 170                 175

Val Lys Glu Tyr Asp Leu Glu Lys His Ala Leu Asp Tyr Lys Asp Thr
        180                 185                 190

Cys Gln Ile Ser Cys Gly Asn Thr Arg Asp Phe Ile Asp Lys Lys Ile
        195                 200                 205

Phe Asp Lys Asn Arg Leu Cys Leu His Leu Phe Ser Glu Met Trp Lys
    210                 215                 220

Ile Tyr Lys Met Asn Lys Asn His Phe Tyr Lys Ser Cys Ile Tyr Gly
225                 230                 235                 240

Phe Leu Leu Gln Lys His Asn Ile Leu Asp Leu Cys Leu Lys Leu Asn
                245                 250                 255

Tyr Asn Leu Ser Phe Cys Asp Lys His Tyr Asp Lys Phe Leu Pro Phe
            260                 265                 270

Ile Asn Ile Lys Asn Lys Ile Arg Phe Tyr Phe Arg His Pro Lys Lys
        275                 280                 285

Ile Phe Lys Lys Asn Asn Ala
    290                 295

<210> SEQ ID NO 3
<211> LENGTH: 283
<212> TYPE: PRT
<213> ORGANISM: Campylobacter jejuni
<220> FEATURE:
<223> OTHER INFORMATION: Campylobacter jejuni ATCC 43429
      alpha-1,4-galactosyltransferase (Campylobacter
      glycosyltransferase D, CgtD)

<400> SEQUENCE: 3

Met Lys Gln Glu Ile Ser Ser Phe Trp Tyr Thr Pro Arg Gly Tyr Lys
1               5                   10                  15

Gly Ile Gly Leu Met Glu Leu Leu Ser Ile Lys Ser Phe Ile Asp Asn
            20                  25                  30

Gly Tyr Lys Phe Ile Leu Tyr Thr Tyr Asn Leu Asp Asp Lys Ile Phe
        35                  40                  45

Lys Lys Leu Asp Glu Leu Phe Asp Asp Phe Glu Leu Lys Asp Ala Asn
    50                  55                  60

Glu Ile Val Ser Phe Lys Asn Tyr Phe Arg Asp Asp Arg Gly Ser Gly
65                  70                  75                  80

Val Ala Ala Phe Ser Asp Tyr Phe Arg Tyr Asn Leu Leu Tyr Leu Lys
                85                  90                  95

Lys Lys Lys Arg Gly Gly Val Trp Val Asp Leu Asp Met Ile Cys Leu
            100                 105                 110

Asn Tyr Ile Asp Leu Asn Glu Glu Tyr Ile Phe Thr Gln Glu Val Asp
        115                 120                 125

Glu Asp Asn Lys Lys Ser Arg Ile Thr Thr Ser Phe Leu Lys Phe Ser
    130                 135                 140

Arg Tyr Ser Asp Phe Gly Lys Asn Leu Ile Gln Glu Ala Glu Lys Ile
145                 150                 155                 160

Ile Asn Lys Arg Lys Lys Ile Ser Trp Gly Val Ile Gly Pro Trp Phe
                165                 170                 175

Leu Ala Asp His Val Lys Lys Cys Gly Leu Glu Asn Phe Val Trp Asp
            180                 185                 190

Tyr Lys Arg Thr Cys Gln Ile Pro Trp Cys Asn Val Lys Ile Phe Leu
        195                 200                 205

Asp Asn Thr Ser Ile Asp Ile Ser Gln Pro Phe Leu His Leu Phe Ser
    210                 215                 220
```

```
Glu Met Trp Arg Leu Asn Asn Met Glu Lys Asn Thr Phe His Gln Met
225                 230                 235                 240

Gly Val Tyr Gly Gln Leu Leu Lys Lys His Glu Ile Glu Lys Leu Tyr
                245                 250                 255

Asn Gln Ile Asn Thr Cys Leu Lys Thr Ser Met Leu Asp Asn Ile Ala
            260                 265                 270

Ser Phe Leu Thr Lys Phe Phe Ile Lys Lys Leu
            275                 280
```

<210> SEQ ID NO 4
<211> LENGTH: 283
<212> TYPE: PRT
<213> ORGANISM: Campylobacter jejuni
<220> FEATURE:
<223> OTHER INFORMATION: Campylobacter jejuni ATCC 43430 alpha-1,4-galactosyltransferase (Campylobacter glycosyltransferase D, CgtD)

<400> SEQUENCE: 4

```
Met Lys Gln Glu Ile Ser Ser Phe Trp Tyr Thr Pro Arg Gly Tyr Lys
 1               5                  10                  15

Gly Ile Gly Leu Met Glu Leu Leu Ser Ile Lys Ser Phe Ile Asp Asn
                20                  25                  30

Gly Tyr Lys Phe Ile Leu Tyr Thr Tyr Asn Leu Asp Asp Lys Ile Phe
            35                  40                  45

Lys Lys Leu Asp Glu Leu Phe Asp Asp Phe Glu Leu Lys Asp Ala Asn
 50                  55                  60

Glu Ile Val Ser Phe Lys Asn Tyr Phe Arg Asp Asp Arg Gly Ser Gly
 65                  70                  75                  80

Val Ala Ala Phe Ser Asp Tyr Phe Arg Tyr Asn Leu Leu Tyr Leu Lys
                85                  90                  95

Lys Lys Lys Arg Gly Gly Val Trp Val Asp Leu Asp Met Ile Cys Leu
            100                 105                 110

Asn Tyr Ile Asp Leu Asn Glu Glu Tyr Ile Phe Thr Gln Glu Val Asp
            115                 120                 125

Glu Asp Asn Lys Lys Ser Arg Ile Thr Thr Ser Phe Leu Lys Phe Ser
130                 135                 140

Arg Tyr Ser Asp Phe Gly Lys Asn Leu Ile Gln Glu Ala Glu Lys Ile
145                 150                 155                 160

Ile Asn Lys Arg Lys Lys Ile Ser Trp Gly Val Ile Gly Pro Trp Phe
                165                 170                 175

Leu Ala Asp His Val Lys Lys Cys Gly Leu Glu Asn Phe Val Trp Asp
            180                 185                 190

Tyr Lys Arg Thr Cys Gln Ile Pro Trp Cys Asn Val Lys Ile Phe Leu
        195                 200                 205

Asp Asn Thr Ser Ile Asp Ile Ser Gln Pro Phe Leu His Leu Phe Ser
210                 215                 220

Glu Met Trp Arg Leu Asn Asn Met Glu Lys Asn Thr Phe His Gln Met
225                 230                 235                 240

Gly Val Tyr Gly Gln Leu Leu Lys Lys His Glu Ile Glu Lys Leu Tyr
                245                 250                 255

Asn Gln Ile Asn Thr Cys Leu Lys Thr Ser Met Leu Asp Asn Ile Ala
            260                 265                 270

Ser Phe Leu Thr Lys Phe Phe Ile Lys Lys Leu
            275                 280
```

```
<210> SEQ ID NO 5
<211> LENGTH: 300
<212> TYPE: PRT
<213> ORGANISM: Artificial Sequence
<220> FEATURE:
<223> OTHER INFORMATION: Description of Artificial Sequence:
      Campylobacter jejuni alpha-1,4-galactosyltransferase
      (Campylobacter glycosyltransferase D, CgtD)
      consensus sequence

<400> SEQUENCE: 5

Met Lys Gln Glu Ile Ser Ser Phe Trp Tyr Thr Pro Arg Gly Tyr Lys
  1               5                  10                  15

Gly Ile Gly Leu Met Glu Leu Leu Ser Ile Lys Ser Phe Ile Asp Asn
             20                  25                  30

Gly Tyr Lys Phe Ile Leu Tyr Thr Tyr Asn Leu Asp Asp Lys Ile Phe
         35                  40                  45

Lys Lys Leu Asp Glu Leu Phe Asp Asp Phe Glu Leu Lys Asp Ala Asn
     50                  55                  60

Glu Ile Val Ser Phe Lys Asn Tyr Phe Arg Asp Asp Arg Gly Ser Gly
 65                  70                  75                  80

Val Ala Ala Phe Ser Asp Tyr Phe Arg Tyr Asn Leu Leu Tyr Leu Lys
                 85                  90                  95

Lys Lys Lys Arg Gly Gly Val Trp Val Asp Leu Asp Met Ile Cys Leu
            100                 105                 110

Asn Tyr Ile Asp Leu Asn Lys Glu Glu Tyr Ile Phe Thr Gln Glu Val
        115                 120                 125

Asp Glu Asp Asn Lys Lys Ser Arg Ile Thr Thr Ser Phe Leu Lys Phe
    130                 135                 140

Ser Arg Tyr Ser Asp Phe Gly Lys Asn Leu Ile Gln Glu Ala Glu Lys
145                 150                 155                 160

Ile Ile Asn Lys Arg Lys Lys Ile Ser Trp Gly Val Ile Gly Pro Trp
                165                 170                 175

Phe Leu Ala Asp His Val Lys Lys Cys Gly Leu Glu Asn Phe Val Trp
            180                 185                 190

Asp Tyr Lys Arg Thr Cys Gln Ile Pro Trp Cys Asn Val Lys Ile Phe
        195                 200                 205

Leu Asp Asn Thr Ser Ile Asp Ile Ser Gln Pro Phe Leu His Leu Phe
    210                 215                 220

Ser Glu Met Trp Arg Leu Asn Asn Met Glu Lys Asn Thr Phe His Gln
225                 230                 235                 240

Met Gly Val Tyr Gly Gln Leu Leu Lys Lys His Glu Ile Glu Lys Leu
                245                 250                 255

Tyr Asn Gln Ile Asn Thr Cys Leu Lys Thr Ser Asp Lys Met Leu Asp
            260                 265                 270

Asn Ile Ala Ser Phe Leu Asn Ile Lys Asn Lys Thr Lys Phe Phe Ile
        275                 280                 285

Lys Lys Leu Lys Lys Ile Phe Lys Asn Asn Ala
    290                 295                 300

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence:"FLAG tag"
      epitope tag

<400> SEQUENCE: 6
```

-continued

```
Asp Tyr Lys Asp Asp Asp Lys
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:
      hexahistidine affinity tag, polyhistidine epitope tag,
      purification tag, six adjacent histidines

<400> SEQUENCE: 7

His His His His His His
  1               5

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence:PCR
      amplification primer CJ-636

<400> SEQUENCE: 8
taaaaggcta catatgactg aaatttcaag tttttgg                               37

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence:PCR
      amplification primer CJ-639

<400> SEQUENCE: 9
ggcaagatga ttgtcgactt aggcattgtt tttc                                  34

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:PCR
      amplification primer CJ42, primer in
      heptosylTase-II

<400> SEQUENCE: 10
gccattaccg tatcgcctaa ccagg                                            25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:PCR
      amplification primer CJ43, primer in
      heptosylTase-I

<400> SEQUENCE: 11
aaagaatacg aatttgctaa agagg                                            25

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence:DDDDK EC5
      purification tag, epitope tag
```

```
<400> SEQUENCE: 12

Asp Asp Asp Asp Lys
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence:purification
      tag, epitope tag peptide derived from Polyoma
      middle T protein

<400> SEQUENCE: 13

Glu Tyr Met Pro Met Glu
 1               5
```